(12) United States Patent
Saigo et al.

(10) Patent No.: US 6,342,636 B1
(45) Date of Patent: Jan. 29, 2002

(54) PROCESS FOR PREPARING OPTICALLY ACTIVE AMINES AND OPTICALLY ACTIVE CARBOXYLIC ACIDS, AND INTERMEDIATES FOR PREPARATION

(75) Inventors: Kazuhiko Saigo; Yukihiko Hashimoto; Kazushi Kinbara, all of Tokyo; Yoshiko Harada, Kawasaki; Kenichi Sakai, Kitaibaraki, all of (JP)

(73) Assignee: Yamakawa Chemical Industry Co., Ltd., Tokyo (JP)

( * ) Notice: Subject to any disclaimer, the term of this patent is extended or adjusted under 35 U.S.C. 154(b) by 0 days.

(21) Appl. No.: 09/181,931

(22) Filed: Oct. 28, 1998

(30) Foreign Application Priority Data

Nov. 6, 1997 (JP) .............................................. 9-304730
Nov. 7, 1997 (JP) .............................................. 9-305627

(51) Int. Cl.[7] ............................................. C07C 211/00
(52) U.S. Cl. ...................... 564/384; 562/490; 562/494
(58) Field of Search ................................ 562/490, 494; 564/384

(56) References Cited

U.S. PATENT DOCUMENTS

| 3,892,803 A | * | 7/1975 | Diamond et al. | ............ 564/172 |
| 3,931,269 A | * | 1/1976 | Diamond et al. | ............ 558/230 |
| 5,066,826 A | * | 11/1991 | Nohira et al. | ............ 560/60 |
| 5,629,450 A | * | 5/1997 | Hijiya et al. | ............ 564/425 |
| 5,856,579 A | * | 1/1999 | Takemoto et al. | ............ 564/425 |

OTHER PUBLICATIONS

Saigo et al, (2–Naphthyl)glycolic acid: a tailored resolving agent for p–sub. 1–arylethylamines, Tetrahedron: Asymmetry, p 2219–2222, Jul. 3, 1998.*

* cited by examiner

Primary Examiner—Gary Geist
Assistant Examiner—Taylor V. Oh
(74) Attorney, Agent, or Firm—Kubovcik & Kubovcik

(57) ABSTRACT

Disclosed is a process for preparing an optically active 1-aryl- or 2-aryl-alkylamines of formulas Ia, Ib and Ic with high optical purity and high yield. The process uses an optically active 1- or 2-naphthylglycolic acid of the general formula II as a resolving agent. Also disclosed is a process for praparing an optically active 1- or 2-naphthylglycolic acid of formula II using an optically active 1-aryl- or 2-aryl-alkylamines of formulas Ia, Ib and Ic as the resolving agents

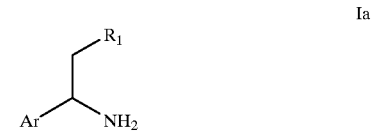

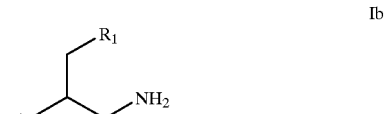

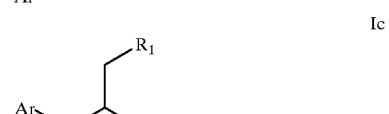

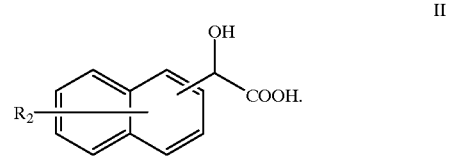

6 Claims, No Drawings

PROCESS FOR PREPARING OPTICALLY ACTIVE AMINES AND OPTICALLY ACTIVE CARBOXYLIC ACIDS, AND INTERMEDIATES FOR PREPARATION

BACKGROUND OF THE INVENTION

The present invention concerns a process for optical resolution of racemic 1-aryl- and 2-aryl-alkylamines including various compounds with an optically active naphthylglycolic acid. The invention also concerns a process for optical resolution of racemic 1- and 2-naphthylglycolic acid with 1-aryl- or 2-aryl-alkylamine. The invention encompasses novel diastereomeric salts, which are formed as the intermediate compounds in the process of optical resolution of 1-aryl- or 2-aryl-alkylamines, or 1- or 2-naphthylglycolic acids.

1-Aryl- and 2-aryl-alkylamines have been used as starting materials or intermediates for production of various medicines and chemicals, and further, known as resolving agents for optical resolution. Examples of such use of 1-arylalkylamines are as follows:

1-(m-Methoxyphenyl)ethylamine is used as a material for brain function improving medicine. 1-(p-Methylphenyl)ethylamine is a resolving agent for 2-hydroxyl-4-phenylbutanoic acid, which is the intermediate for angiotensin converting enzyme inhibitors such as Cilazapril, Enalapril and Benazepril and also a resolving agent for cis-permethric acid, which is a material for an insecticide. 1-(p-Chlorophenyl)ethylamine is known to be useful as a material for a bactericide in agricultural use. It is expected that use of these arylalkylamines will develop further in the future.

For the optical resolution of racemates of these amines there has been employed diastereomeric salt process, because of easy application thereof to industrial production and good reproducibility. With respect to the resolution by diastereomeric salt formation, even in the limited scope of combinations of amines and carboxylic acids, statistic data as of around 1981 shows that more than 2500 cases have been reported. [P. Newman, "Optical Resolution Procedures for Chemical Compounds", vol. 1 and 2 (1981), Optical Resolution Information Center, Manhattan College, Riverdale, N.Y.] Though such a large number of experimental results have been reported, as pointed out by Jacques et al [J. Jacques et al., "Enantiomers, Racemates, and Resolutions", John Willy & Sons, New York, Chichester, Brisbane, Toronto (1981) p.380] and Sheldon [R. Sheldon, "Chirotechnology-Industrial Synthesis of Optically Active Compounds", Marcel Dekker, Inc., New York, Basel, Hong Kong (1993) p.20], when a novel compound is; to be resolved, there is no reliable principle or theory for choosing the resolving agent, and it is inevitable to seek the resolving agent by trial and error.

Therefore, in order to resolve a racemate of this kind of amines, it has been necessary to carry out a search for a suitable resolving agent by a trial and error method, which is of course troublesome and requires a lot of time. There has been thus a strong demand, in the field of diastereomeric salt method of optical resolution, for either standards of choosing suitable resolving agents for, more specifically, acidic resolving agents which may be applied to the racemates of a wide range of amines.

The inventors resolved 1-arylalkylamines using various hydroxycarboxylic acids as the resolving agents. The results are summarized in Table 1 below. In the row of the resolving agents, the hydroxycarboxylic acids, in Table 1, "A" stands for mandelic acid, "B" for p-methylmandelic acid, "C" for p-methoxymandelic acid, "D" for 2-hydroxyphenylpropionic acid, "E" for 2-hydroxyphenylbutanoic acid and "F" for 3-hydroxy-2-phenylpropionic acid. Chemical structures of these compounds are shown below.

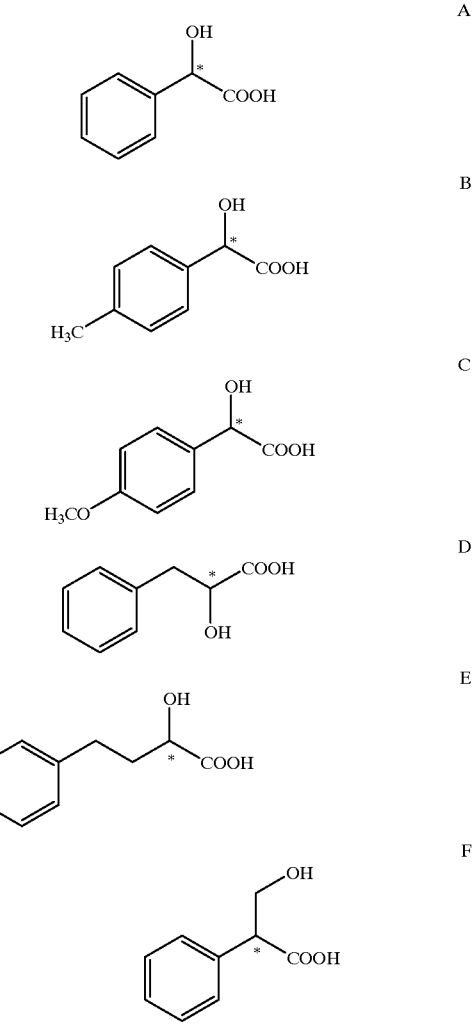

TABLE 1

Optical Resolution of 1-Arylalkylamines (formula Ia) with Acidic Resolving Agents

| Run No. | Resolving Agent | $R_3$ | $R_1$ | Yield (%) | Optical Purity D % | Resolving Efficiency E % |
|---|---|---|---|---|---|---|
| 1 | A | H | H | 76 | 87 | 66 |
| 2 | A | o-methyl | H | 71 | 100 | 71 |
| 3 | A | o-methoxy | H | 69 | 81 | 56 |
| 4 | A | o-Cl | H | 76 | 29 | 22 |
| 5 | A | m-methyl | H | 94 | 12 | 11 |
| 6 | A | m-Cl | H | 59 | 38 | 22 |
| 7 | A | m-methoxy | H | 69 | 89 | 62 |
| 8 | A | p-methyl | H | 88 | 4 | 4 |
| 9 | A | p-methoxy | H | 84 | 4 | 3 |
| 10 | A | p-Cl | H | 109 | 2 | 2 |
| 11 | A | H | p'-tolyl | 84 | 97 | 73 |
| 12 | B | H | H | 74 | 80 | 59 |

TABLE 1-continued

Optical Resolution of 1-Arylalkylamines (formula Ia)
with Acidic Resolving Agents

| Run No. | Resolving Agent | $R_3$ | $R_1$ | Yield (%) | Optical Purity D % | Resolving Efficiency E % |
|---|---|---|---|---|---|---|
| 13 | B | p-methyl | H | 85 | 63 | 54 |
| 14 | C | H | H | 70 | 89 | 62 |
| 15 | C | m-methyl | H | 76 | 75 | 57 |
| 16 | C | p-methyl | H | 72 | 85 | 61 |
| 17 | C | p-methoxy | H | 62 | 46 | 29 |
| 18 | D | H | H | 49 | 85 | 41 |
| 19 | D | p-methyl | H | no crystal obtainable | | |
| 20 | D | H | methyl | no crystal obtainable | | |
| 21 | E | H | H | 110 | 80 | 88 |
| 22 | E | p-methyl | H | 77 | 85 | 65 |
| 23 | E | p-methoxy | H | 98 | 54 | 53 |
| 24 | E | H | methyl | oily substance occurred | | |
| 25 | F | H | H | 81 | 3 | 2 |

*Resolution Efficiency E = Yield × Optical Purity (%)

From the results shown in Table 1 the following was concluded:

(1) Resolving agent "A" resolves non-substituted and some of o- or m-substituted 1-arylalkylamines, but does not resolve p-substituted amines at all.

(2) Resolving agents "B" and "C" which have substituent at p-position resolve non-substituted, and m- and p-substituted 1-arylalkylamines with relatively high resolving efficiency. Optical purities of the products are generally low.

(3) Resolving agents "D" and "E" which have one or two methylene groups in the molecules resolve non-substituted and p-substituted 1-arylalkylamines. Optical purities of the products are also low.

(4) Resolving agent "F" which has a hydroxy group at the β-position does not resolve non-substituted 1-arylalkylamines, which are resolved by other a-hydroxycarboxylic acids.

The above conclusion can be summarized as follows: The non-substituted 1-arylalkylamines can be resolved with any of α-hydroxycarboxylic acids, the o-substituted 1-arylalkylamines can be resolved with non-substituted α-hydroxycarboxylic acid (resolving agent "A"); the m-substituted 1-arylalkylamines can be resolved with non-substituted or p-substituted α-hydroxy-carboxylic acids; and p-substituted 1-arylalkylamines can be resolved with p-substituted α-hydroxycarboxylic acids. On the other hand, there is no effective resolving agent for the 1-(o-, m-, p-halogen-substituted aryl)alkylamines.

Based on the above experimental results we reached the final conclusion that optical resolution can be carried out by choosing the hydroxycarboxylic acids used as the resolving agents having such molecular structures that are similar to those of 1-arylalkylamines to be resolved, in other words, by choosing a resolving agent of substantially equal molecular length to that of the substrates [K. Kinbara et al., Tetrahedron Asymmetry, 7(6),1539 (1996)] Correctness of this rule based on experience was proved by X-ray crystal structure analysis of the obtained diastereomeric salts [K. Kinbara et al., J. Chem. Soc., Perkin Trans. 2, 1996, 2615].

However, in the optical resolutions using the known substituted hydroxycarboxylic acids as the resolving agents shown in Table 1 optical purities of the products are low except for some minor cases, and therefore, it is necessary to improve the optical purities of the products by, for example, repeating recrystallization of the diastereomeric salts. This is of course a disadvantageous factor of the processes.

The inventors continued to make efforts, on the basis of the above knowledge, in finding resolving agents which may be commonly effective for optical resolution of 1-aryl- and 2-aryl-alkylamines inclusive of m- and p-substituted 1-arylalkylamines which could not have been resolved by the known technologies. As a result, the inventors discovered the facts that non-substituted and substituted 1- or 2-naphthyl-glycolic acids are useful as the novel resolving agents and that these resolving agents very efficiently resolve amines which could not have been resolved with known resolving agents or optical purities of which were low, particularly, the amine derivatives having a substituent of an alkyl group, alkyloxy group or halogen atom at m-position or p-position. It has been believed that, in optical resolution of halogen-substituted derivatives, efficient resolution could be done only when a homologous or corresponding halogen-substituted hydroxy-carboxylic acid is used as the resolving agent. The above fact that even a non-homologous resolving agent can resolve the halogen-substituted 1-aryl- or 2-aryl-alkylamines is a surprising discovery.

SUMMARY OF THE INVENTION

An object of the present invention is to utilize the above knowledge obtained by the inventors and to provide an efficient process for optical resolution of racemic 1-aryl- and 2-aryl-alkylamines in a wide range of chemical structure using novel resolving agents, optically active 1- or 2-naphthylglycolic acids.

Another object of the present invention is to provide an efficient process for optical resolution in the reversed relation of the resolving agents and the substrates to that noted above, i.e., resolution of racemic substituted or non-substituted 1- or 2-naphthylglycolic acids using an optically active 1-aryl- or 2-aryl-alkylamine as a resolving agent.

DETAILED EXPLANATION OF THE PREFERRED EMBODIMENTS

The process for preparing optically active 1-arylalkylamines according to the present invention comprises the steps of: combining racemic 1-arylalkylamine expressed by formula Ia:

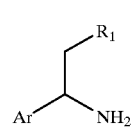

Ia

[in formula Ia, Ar stands for a substituted or non-substituted phenyl group or a substituted or non-substituted naphthyl group; having one of the following formulas

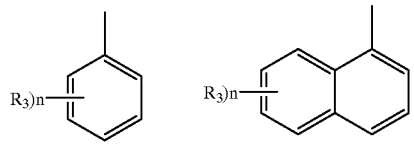

where $R_3$ is a $C_1$–$C_5$ straight or branched chain alkyl or alkyloxy group, chlorine atom, bromine atom, iodine atom or nitro group and n is zero, one, two or more; R1 stands for hydrogen atom, a $C_1$–$C_5$ straight or branched chain alkyl or alkyloxy group, or substituted phenyl group, the substituent of the phenyl group is a $C_1$–$C_5$ straight or branched chain alkyl or alkyloxy group, chlorine atom, bromine atom, iodine atom or nitro group, and may be two or more.]

with an optically active 1-naphthylglycolic acid or 2-naphthylglycolic acid, or one of their derivatives expressed by the general formula II below:

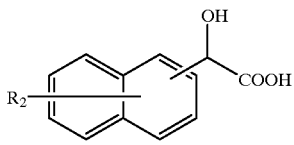

II

[in formula II, $R_2$ stands for a $C_1$–$C_5$ straight or branched chain alkyl or alkyloxy group, chlorine atom, bromine atom, iodine atom or nitro group, and may be two or more.]

and then, decomposing the diastereomeric salt thus obtained to isolate the optically active 1-arylalkylamine.

The process for preparing an optically active 2-arylalkylamine according to the present invention comprises the steps of: combining a racemic 2-arylalkylamine expressed by formula Ib or Ic:

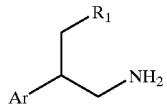

Ib

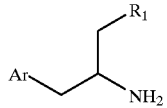

Ic

[in formulas Ib and Ic, Ar and $R_1$ have the meaning defined above.]

with an optically active 1-naphthylglycolic acid or 2-naphthylglycolic acid, or one of their derivatives, expressed by the general formula II below:

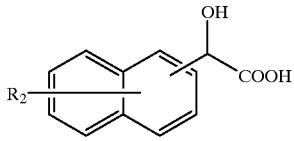

II

[in formula II, $R_2$ has the meaning defined above.] and then, decomposing the diastereomeric salt thus obtained to isolate the optically active 2-arylalkylamine.

The process for preparing an optically active naphthylglycolic acid according to the present invention comprises the steps of: combining a racemate of 1-naphthylglycolic acid or 2-naphthylglycolic acid expressed by formula II:

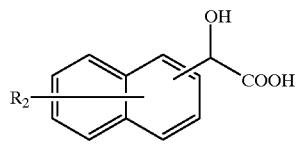

II with an optically active 1-arylalkylamine expressed by general formula Ia or an optically active 2-arylalkylamine expressed by general formulas Ib or Ic

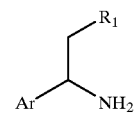

Ia

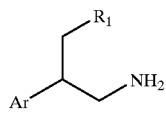

Ib

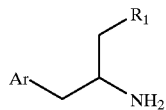

Ic

[in the formulas, Ar and $R_1$ have the meaning defined above.] and then, decomposing a diastereomeric salt thus obtained to isolate an optically active 1-naphthylglycolic acid, 2-naphthylglycolic acid or a derivative thereof.

Diastereomeric salts which are formed during the above process for preparing the optically active isomers and expressed by general formula IIIa, IIIb and IIIc:

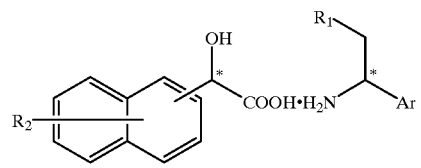

IIIa

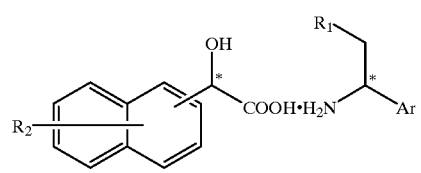

IIIb

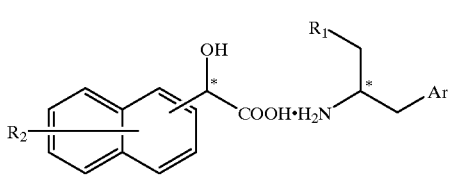

IIIc

[In the formulas, $R_1$ and $R_2$ has the meaning defined above; and * indicates position of the asymmetric carbon atom.] are novel compounds and constitute a part of the present invention.

In both the processes of the present invention, i.e,.the process where racemates of 1-aryl- or 2-aryl-alkylamines are resolved with an optically active substituted or non-substituted 1- or 2-naphthylglycolic acid as the resolving agent, and the process where racemates of substituted or non-substituted 1- or 2-naphthylglycolic acids are resolved with an optically active 1-aryl- or 2-aryl-alkylamine as the resolving agent, various solvents can be used as the reaction medium. Examples of the solvents are: a lower alcohol such as methanol, ethanol, 2-propanol, 1-propanol and 1-butanol; water; ethers; ketones such as acetone, MEK and MIBK; and a mixture of any of these solvents. Particularly, absolute alcohols and water-containing alcohols are preferable.

The resolving agents or the optically active compounds are used in such an amount that the molar ratio of the resolving agent to the substrates to be resolved is in the range of 0.2–1.2. Preferable range in molar ratio is 0.5–1.0.

In order to obtain the diastereomeric salts, in either cases where an amine is a substrate and a carboxylic acid is a resolving agent or where a carboxylic acid is a substrate and an amine is a resolving agent, both of the reactants are charged in a reaction medium and heated to a temperature of the boiling point of the medium or lower. Then, the reaction mixture is cooled down to precipitate the diastereomeric salt, which is isolated. It is preferable to seed crystals of the desired salt for the purpose of precipitating a salt of a higher optical purity. The combinations of the substrates and resolving agents according to the present invention generally give the salts of high optical purities. It is, however, of course preferable to use an appropriate quantity of the reaction medium and to cool down slowly from the temperature of the state of solution so as to avoid rapid precipitation and to cause precipitation of fully grown salt crystal. Solid/liquid separation can be carried out using an ordinary filter or a centrifuge. Rinsing the salt crystal with a suitable solvent during the separation to remove the mother liquor will give a salt of improved optical purity. The diastereomeric salt thus obtained can be refined by recrystallization from a suitable solvent to give the salt having a better optical purity.

The above diastereomeric salt may be easily subjected to double decomposition by adding an acid or an alkali, and the desired optically active compounds can be recovered. The optically active compounds will be obtained in a pure state by recrystallization in the case where an optically active naphthylglycolic acid is aimed at and distillation in the case where an optically active 1-aryl- or 2-aryl-alkylamine is targeted.

As the processes for preparing the racemates of substituted or non-substituted 1- or 2-naphthylglycolic acids, the following processes are known:
1. Bromination or chlorination of 2-acetonaphthone, the starting material, in a reaction medium to form an ω-dihalide. The product is hydrolyzed, and then the reaction mixture is acidified [Schweitzer, Chem. Ber., 24 547 (1891)] This process can be carried out using 1-acetonaphthone as the starting material.
2. Reaction of naphthalene-1- or -2-aldehyde with bromoform and potassium hydroxide [Edward L. Compere Jr., J. Org. Chem., 33 2565–6 (1968)]
3. Reduction of naphthylglyoxylic acid (α-oxonaphthalene acetic acid) with sodium amalgam [Bradley, Brindley, J. Chem. Soc., 1622 (1956)] or sodium borohydride.

For preparation of optically active 1- and 2-naphthylglycolic acids the following processes are known:
1. Enzymatic process using naphthalene-2-yl-oxo-acetaldehyde as the starting material [R. Howe et al., J. Med. Chem., 16, 1020 (1973)]
2. Reduction of ketocarboxylic acids in the form of a clathrate compound with β-cyclophane [K. Koga et al., Chem. Pharm. Bull., 33 3571 (1985)]
3. Reduction of the same material as above under clathration by β-cyclodextrine [K. Hattori et al., Bull. Chem. Soc. Jpn., 65 2690 (1992)]

None of the processes, however, are suitable for industrial practice.

The present invention enables production of optically active 1-aryl- and 2-aryl-alkylamines, which are useful as the intermediate compounds for various medicines and resolving agents for preparing the intermediates, with high efficiency or with high optical purities and high yields.

According to the invention resolution of m- or p-substituted or non-substituted 1-aryl- and 2-aryl-alkylamine will be carried out much more easily. Before, resolving agents have been chosen separately in view of the substrates to be resolved. The invention makes it possible to resolve various 1-aryl- or 2-aryl-alkylamines using only one resolving agent. Production of the optically active isomers on an industrial scale is thus facilitated.

EXAMPLES

The following explains the present invention by describing preparation of the material substances and resolving agents, and working examples of the optical resolution.

Optical purities in the preparation and working examples were measured by HPLC. Conditions for the measurement are shown in Table 2.

TABLE 2

| Examples | Object of Measurement | Conditions |
| --- | --- | --- |
| Preparation 2 | 1-naphthylglycolic acid | (1) |
| Preparation 3 | 2-naphthylglycolic acid | (2) |
| | 1-arylalkylamine $R_3$ = | |
| Resolution 1 | H | (3) |
| Resolution 2 | m-Br | (4) |
| Resolution 3 | m-methoxy | (4) |
| Resolution 4 | p-methyl | (4) |
| Resolution 5 | p-ethyl | (4) |
| Resolution 6 | p-n-propyl | (5) |
| Resolution 7 | p-methoxy | (4) |
| Resolution 8 | p-cyclohexyl | (5) |
| Resolution 9 | p-$NO_2$ | (5) |
| Resolution 10 | p-Cl | (4) |
| Resolution 11 | p-Br | (5) |
| Resolution 12 | 1-(1-naphthyl)ethylamine | (6) |
| Resolution 13 | | (3) |
| Resolution 14 | | (3) |

| Conditions | Column | Eluent Solution | Detecting Wave Length (nm) |
| --- | --- | --- | --- |
| (1) | CHIRALCEL OJ-R | aq. perchloric acid (pH 2.0):acetonitrile = 9:1 | 254 |
| (2) | CHIRALCEL OJ-R | aq. perchloric acid (pH 2.0):acetonitrile = 4:1 | 254 |
| (3) | CROWNPAK CR(+) | aq. perchloric acid | 210 |
| (4) | CHIRALCEL OJ-R | 0.2 M sodium perchlorate: methanol = 19:1 | 210 |
| (5) | CHIRALCEL OJ-R | 0.2 M sodium perchlorate: methanol = 10:1 | 210 |
| (6) | CHIRALCEL OJ-R | 0.2 M sodium perchlorate: acetonitrile = 4:1 | 254 |

Preparation 1

Synthesis of 1-naphthylglycolic acid

Under argon atmosphere distilled 1,4-dioxane (100 mL) and distilled water (100 mL) were charged in a two neckedflask in an ice bath. To the flask 1-naphthaldehyde (15.6 g, 0.1 mol), lithium chloride (8.48 g, 0.2 mol) and potassium hydroxide (22.4 g, 0.4 mol) were added. After stirring at 0° C. for 5 minutes, bromoform (25.2 g, 0.1 mol) was added, and stirring was continued for a further 1 hour at the same temperature. Completion of the reaction was ascertained by TLC, and then, water (100 mL) was added to the reaction mixture. After rinsing three times with ether (each 70 mL), pH of the aqueous phase was decreased to 2 with conc. hydrochloric acid under ice cooling. The aqueous phase was subjected to extraction of five times with ether (each 100 mL), and the organic phase thus formed was rinsed once with saturated sodium chloride solution and once with distilled water. The organic phase was dried over anhydrous magnesium sulfate (80 g) and the solvent was distilled off under reduced pressure. The residue was dried under vacuum, and 16.0 g (yield: 79%) of the target compound was obtained. The product, without being purified, was used as the material for optical resolution described below.

Preparation 2

Optical Resolution of 1-naphthylglycolic acid

The crude 1-naphthylglycolic acid prepared in the above example (16 g) and cinchonine (12 g, corresponding to 0.5 equivalent of the acid), were heated with ethanol (700 mL) to the refluxing temperature for 2 hours. The reaction solution was cooled down and the precipitated crystal of diastereomeric salt was separated by filtration (product: 7.87 g, yield: 39%). Ethanol (300 mL) was added to the crystal and refluxing was repeated for further 2 hours. After cooling down the crystal formed was separated by filtering (product: 5.32 g, yield: 68%, overall yield through the preceding step: 27%, optical purity: 100% e.e.)

The purified diastereomeric salt was decomposed by an ordinary method to give crystal of the optically active 1-naphthylglycolic acid.

Melting point: 125.0–127.5° C. $[\alpha]_D^{14}$+162° (c 1.203, $H_2O$); IR $(cm^{-1})$ 3300–3450, 2800–3250, 1759, 1692, 1228, 793, 777; $^1$H-NMR (DMSO) δ (ppm) 5.67 (s, 1H); 5.90–6.15 (s, 1H); 7.45–7.57 (m, 3H); 7.57–7.62 (d, 1H); 7.85–7.90 (d, 1H); 7.91–7.95 (m, 1H); 8.26–8.32 (m, 1H); 12.5–12.8 (s, 1H).

Preparation 3

Synthesis of 2-naphthylglycolic acid

2-Acenaphthone (150 g) was added to acetic acid (400 mL) under stirring, and the mixture was heated (up to 60° C.) to dissolution. Chlorine gas was introduced into the solution to form ω-dichloride. When the reaction was completed, the reaction solution was poured on water (1 L), and the precipitated crystal was separated and dried. The dried crystal was recrystallized from a mixed solvent of hexane (300 mL) and chloroform (70 mL) to give purified ω-dichloride (179 g, yield: 85%). Into the solution of sodium hydroxide (116 g) in water (1 L) and heated to 50° C. the above refined ω-dichloride (175 g) was added gradually over two hours to hydrolyze it. After the addition and subsequent stirring for one hour, conc. hydrochloric acid (100 mL) was added to acidify the solution, and the acidic solution was subjected to extraction with ether (4.5 L). The separated ether phase was dried over anhydrous sodium sulfate, and the solvent was distilled off to obtain crude crystal of (RS)-2-naphthylglycolic acid. The crude crystal was recrystallized from a mixed solvent of chloroform (600 mL) and ethanol (50 mL) to give purified crystal of (RS)-2-naphthylglycolic acid (83 g, yield: 56%).

Melting point: 164.0–166.5° C. IR $(cm^{-1})$ 3600–2400, 1722, 1223, 830, 815, 742; $^1$H-NMR (DMSO) δ (ppm) 5.26 (s, 1H); 7.50–7.62 (m, 3H); 7.89–7.98 (m, 4H).

Optical Resolutions 1–11

Resolution of (RS)-1-arylalkylamines with optically active 2-naphthylglycolic acid Example 1

Resolution of 1-phenylethylamine

A solution of (RS)-1-phenylethylamine (382 mg) in a mixed solvent of ethanol (5.0 mL) and water (0.5 mL) was charged in a reaction vessel, to which (S)-2-naphthylglycolic acid (625 mg) was added, and the mixture was heated to dissolve. After complete dissolution the solution was stirred for 5 minutes, and the vessel was placed in a thermostatted bath kept at 40° C. and stood still. Two hours later temperature of the thermostatic chamber was decreased to 30° C. and let as it goes. Precipitated crystal was separated and dried. A diastereomeric salt was obtained (304 mg, yield: 61%).

Melting point: 177.5–180.0° C. $[\alpha]_D^{24.4}$+58.7° (c 0.50, EtOH) IR $(cm^{-1})$ 3600–3200, 3200–2800, 1608, 1575, 1530, 1381, 860, 812, 746; $^1$H-NMR (DMSO) δ (ppm) 1.43(d, 3H); 4.28 (q, 1H); 4.71 (s, 3H); 7.31–7.58; 7.77–7.86 (m, 12H).

The salt obtained above was decomposed by addition of 1N-hydrochloric acid, and the decomposition mixture was subjected to extraction with ether. Sodium hydroxide was added to the aqueous phase to increase pH to 11 or higher, and then the target amine was extracted with chloroform. The organic phase was dried over anhydrous sodium sulfate, and then, the solvent was distilled off. (S)-1-phenylethylamine (optical purity: 96% e.e.) was obtained as an oily substance.

Example 2

Resolution of 1-(m-methoxyphenyl)ethylamine

Example 1 was repeated using (RS)-1-(m-methoxyphenyl)-ethylamine (428 mg), instead of (RS)-1-phenylethylamine, in the form of a solution in a mixed solvent of ethanol (3.6 mL) and water (0.4 mL), and adding (S)-2-naphthylglycolic acid (572 mg) to the solution. A diastereomeric salt was obtained (339 mg, yield: 68%).

Melting point: 168–170° C. $[\alpha]_D^{24.4}$+62.6° (c 0.49, MeOH); IR $(cm^{-1})$ 3600–3200, 3200–2800, 1610, 1580, 1540, 1382, 860, 815, 755. $^1$H-NMR (DMSO) δ (ppm) 1.41(d, 3H); 3.34 (brs, 4H); 3.73 (s, 3H); 4.26 (q, 1H); 4.70 (s, 1H); 7.28 (t, 1H); 7.42–7.49 (m, 2H); 7.57 (d, 1H); 7.78 (d, 1H); 7.85–7.86 (m, 3H).

The above diastereomeric salt was decomposed as described in Example 1. Extraction as in Example 1 gave (S)-1-(m-ethoxy-phenyl)ethylamine as an oily substance (optical purity: 98% ee).

Example 3

Resolution of 1-(p-n-propylphenyl)ethylamine

Example 1 was repeated using (RS)-1-(p-n-propylphenyl)-ethylamine (313mg), instead of (RS)-1- phenylethylamine, in the form of a solution in a solvent consisting of ethanol (10 mL) and water (1 mL), and adding (S)-2-naphthylglycolic acid (397 mg) to the solution. A diastereomeric salt was obtained (309 mg, yield: 80%).

Melting point: 168–170° C. $[\alpha]_D^{24.4}$+59.4° (c 0.49, MeOH); $^1$H-NMR (DMSO) δ (ppm) 0.88 (t, 3H); 1.421d, 3H); 1.56 (q, 2H); 2.55 (m, 2H); 3.34 (brs, 4H); 4.26 (q, 1H); 4.68 (s, 1H); 7.17 (d, 2H); 7.33 (d, 2H); 7.43–7.48 (m, 2H); 7.57 (d, 1H); 7.68 (d, 1H); 7.85 (m, 3H).

The above diastereomeric salt was decomposed as described in Example 1. Extraction as in Example 1 gave (S)-1-(p-n-propylphenyl)ethylamine as an oily substance (optical purity: 99% e.e. or higher).

Example 4

Resolution of 1-(p-chlorophenyl)ethylamine

Example 1 was repeated using (RS)-1-(p-chlorophenyl)-ethylamine (485 mg), instead of (RS)-1-phenylethylamine, in the form of a solution in a mixed solvent of ethanol (14.0 mL) and water (3.1 mL), and adding (S)-2-naphthylglycolic acid (565 mg) to the solution. A diastereomeric salt was obtained (385 mg, yield: 77%).

Melting point: 218.5–221° C. $[\alpha]_D^{24.4}$+61.10 (c 0.50, MeOH); $^1$H-NMR (DMSO) δ (ppm) 1.40 (d, 3H); 4.29 (q, 1H); 4.74 (s, 1H); 7.39–7.49 (m, 6H); 7.57 (d, 1H); 7.79 (d, 1H); 7.85–7.86 (m, 3H).

The above diastereomeric salt was decomposed as described in Example 1. Extraction as in Example 1 gave (S)-1-(p-chlorophenyl)ethylamine as an oily substance (optical purity: 98% e.e.).

In addition to the above described Examples 1–4 resolution was tried on the racemates of the following amines under the same conditions.

Example 5

1-(m-bromophenyl)ethylamine

Example 6

1-(m-methylphenyl)ethylamine

Example 7

1-(p-ethylphenyl)ethylamine

Example 8

1-(p-methoxyphenyl)ethylamine

Example 9

1-(p-cyclohexylphenyl)ethylamine

Example 10

1-(p-nitrophenyl)ethylamine

Example 11

1-(p-bromophenyl)ethylamine

The results of Examples 1–11 are shown as a whole in Table 3.

TABLE 3

Resolution of 1-Arylalkylamines with Optically Active 2-Naphthylglycolic Acids

| No. | $R_3$ | Yield % | Optical Purity De % | Resolution Efficiency E % |
|---|---|---|---|---|
| 1 | H | 61 | 96 | 59 |
| 2 | m-methoxy | 68 | 98 | 67 |
| 3 | p-n-propyl | 80 | >99 | 79 |
| 4 | p-Cl | 77 | 98 | 75 |
| 5 | m-Br | 91 | 74 | 67 |
| 6 | p-methyl | 81 | 95 | 77 |
| 7 | p-ethyl | 62 | >99 | 61 |
| 8 | p-methoxy | 58 | 87 | 50 |
| 9 | p-cyclohexyl | 50 | 91 | 46 |
| 10 | p-$NO_2$ | 80 | 70 | 56 |
| 11 | p-Br | 91 | 93 | 85 |

Example 12

Resolution of (RS)-1-(1-naphthyl)ethylamine with optically active 2-naphthylglycolic acid A solution of (RS)-1-(1-naphthyl)ethylamine (459 mg) in a mixed solvent of ethanol (4.4 mL) and water (1.6 mL) was charged in a reaction vessel, to which (S)-2-naphthylglycolic acid (565 mg) was added, and the mixture was heated to dissolve. After complete dissolution the solution was stirred for 5 minutes, and the vessel was placed in a thermostatted bath kept at 40° C. Two hours later temperature of the bath was decreased to 30° C. Precipitated crystal was separated and dried. A diastereomeric salt was obtained (376 mg, yield: 75%).

Melting point: 170° C. (decomposing); $[\alpha]_D^{24.4}$+59.2° (c 0.50, MeOH); $^1$H-NMR (DMSO) δ (ppm) 1.54 (d, 3H); 3.40 (brs, 4H); 4.74 (s, 1H); 5.17 (q, 1H); 7.43–7.61(m, 7H); 7.74 (d, 1H); 7.78 (d, 1H); 7.84–7.86 (m, 2H); 7.91 (d, 1H); 7.98 (d, 1H); 8.14 (d, 1H).

The salt obtained above was decomposed by addition of 1N-hydrochloric acid, and the decomposition mixture was subjected to extraction with ether. Sodium hydroxide was added to the aqueous phase to increase pH to 11 or higher, and then the target amine was extracted with chloroform. The organic phase was dried over anhydrous sodium sulfate, and then, the solvent was distilled off. (S)-1-(1-naphthyl) ethylamine was obtained as an oily substance.

Yield: 75% Optical purity: 96% e.e. Resolution Efficiency: 72%.

Example 13

Resolution of (RS)-1-methyl-2-phenylethylamine with optically active 2-naphthylglycolic acid In a reaction vessel (RS)-1-methyl-2-phenylethylamine (133.7 mg) and (R)-2-naphthylglycolic acid (200 mg) were dissolved in 97.5%-ethanol (3.7 mL) under heating. The vessel was placed in a thermostatted bath kept at 40° C. The temperature of the bath was decreased over one hour to 30° C., and the vessel was allowed to stand for 6 hours. Precipitated crystal was separated by filtration and dried. A diastereomeric salt was obtained (160.7 mg, yield: 96%).

Melting point: 179.5–181.5° C. IR ($cm^{-1}$) 3360, 3200–2800, 1569, 1399, 864, 817, 750, 732.

The salt obtained above was decomposed by addition of 1N-hydrochloric acid, and the decomposition mixture was subjected to extraction for three times with ether (each 15 mL). The aqueous phase was cooled to 0°C., and potassium hydroxide was added thereto to increase pH of the solution to about 12. The target amine was extracted three times with methylene chloride (each 20 mL). The organic phase was rinsed twice with water and dried over anhydrous sodium sulfate, and then, the solvent was distilled off. (R)-1-methyl-2-phenylethylamine was obtained as an oily substance (optical purity: 46% e.e.).

Example 14

Resolution of (RS)-2-methyl-2-phenylethylamine with optically active 2-naphthylglycolic acid In a reaction vessel (RS)-2-methyl-2-phenylethylamine (267.9 mg) and (S)-2-naphthylglycolic acid (400 mg) were dissolved in 97.5%-ethanol (8.2 mL) under heating. The vessel was placed in a thermostatted bath kept at 40° C., and the temperature of the bath was decreased over one hour to 30° C. The vessel was allowed to stand for 6 hours. Precipitated crystal was separated by filtration and dried. A diastereomeric salt was obtained (332mg, yield: 99%).

Melting point: 175.0–177.5° C. IR (cm$^{-1}$) 3350, 3200–2800, 1560, 1400, 864, 818, 745.

The salt obtained above was decomposed by addition of 1N-hydrochloric acid (30 mL), and the decomposition mixture was subjected to extraction for three times with ether (each 30 mL). The aqueous phase was cooled to 0° C., and potassium hydroxide was added thereto to increase pH of the solution to about 12. The target amine was extracted three times with methylene chloride (each 30 mL). The organic phase was rinsed twice with water and dried over anhydrous sodium sulfate, and then, the solvent was distilled off. (S)-2-methyl-2-phenylethylamine was obtained as an oily substance (optical purity: 69% e.e.).

Example 15

Resolution of (RS)-1-methyl-2-phenylethylamine with optically active 1-naphthylglycolic acid In a reaction vessel (RS)-1-methyl-2-phenylethylamine (66.9 mg) and (S)-1-naphthylglycolic acid (100 mg) were dissolved in absolute ethanol (1.8 mL) under heating. The vessel was placed in a thermostated bath kept at 40° C., and the temperature of the bath was decreased over one hour to 30° C. The vessel was allowed to stand for 6 hours. Precipitated crystal was separated by filtration and dried. A diastereomeric salt was obtained (81.9 mg, yield: 98%).

Melting point: 174.0–176.0° C. IR (cm$^{-1}$) 3200–2800, 2560, 1540, 1395, 792, 741.

The salt obtained above was decomposed by addition of 1N-hydrochloric acid (10 mL), and the decomposition mixture was subjected to extraction for three times with ether (each 15 mL). The separated aqueous phase was cooled to 0° C., and potassium hydroxide was added thereto to increase pH of the solution to about 12. The target amine was extracted three times with methylene chloride (each 20 mL). The organic phase was rinsed twice with water and dried over anhydrous magnesium sulfate, and then, the solvent was distilled off. (S)-1-methyl-2-phenylethylamine was obtained as an oily substance (optical purity: 50% e.e.).

Example 16

Resolution of (RS)-2-naphthylglycolic acid with optically active 1-phenylethylamine (RS)-2-naphthylglycolic acid (50 g) and (R)-1-phenylethylamine (24 g) were charged in a reaction vessel and ethanol (400 mL) was added thereto, and the mixture was heated to dissolve. After complete dissolution, the solution was stirred for about 5 minutes. The vessel was placed in a thermostated bath kept at 40° C. Two hours later the temperature of the bath was decreased to 30° C., and the vessel was allowed to stand. Precipitated crystal was separated and dried. Crude diastereomeric salt (23.37 g) was obtained. The crude salt was recrystallized twice from 7.5 parts and 6.5 parts of 97%-ethanol, and further, once from 6.6 parts of absolute ethanol to give purified salt (11.39 g, yield: 28%).

Melting point: 181.5–185.5° C. $[\alpha]_D^{25}$–58.0° (c 0.50, MeOH); IR (cm$^{-1}$) 3600–3200, 3200–2800, 1608, 1575, 1530, 1381, 860, 812, 746. $^1$H-NMR (DMSO) δ (ppm) 1.43 (d, 3H); 4.28 (q, 1H); 4.71 (s, 1H); 7.31–7.58; 7.77–7.86 (m, 12H).

The crude salt obtained was decomposed by addition of 3N-hydrochloric acid, and the decomposition mixture was subjected to extraction with ether. The separated ether phase was dried over anhydrous sodium sulfate. The solvent was distilled off and crude (R)-2-naphthylglycolic acid (7.04 g) was obtained in the form of white crystal. The crude product was recrystallized from a mixed solvent of chloroform (30 mL) and ethanol (5 mL) to give purified (R)-2-naphthylglycolic acid (product: 6.28 g, yield: 25%, optical purity: 99% e.e. or higher).

Melting point: 162.0–163.5° C.; $[\alpha]_D^{25}$–143.4° (c 0.98, EtOH); IR (cm$^{-1}$) 3600–2200, 1690, 1400, 1283, 862, 828, 747. $^1$H-NMR (DMSO) δ (ppm) 3.35 (brs, 1H); 5.21(s, 1H); 7.48–7.59 (m, 3H); 7.88–7.95 (m, 4H).

The mother liquor of the above purified diastereomeric salt was concentrated to dryness, and the residue was dissolved in dilute hydrochloric acid. Ether was added to the solution to separate the resolving agent, (R)-1-phenylethylamine, into the aqueous phase. The ether phase was dried and the solvent was distilled off to give dry residue (30.59 g). (S)-1-phenylethylamine (18 g) and ethanol (300 mL) were added to the residue and the mixture was heated to dissolve the solid matter. After complete dissolution the solution was stirred for about 5 minutes and placed in a thermostatted bath kept at 40° C. Two hours later, temperature of the bath was cooled to 30° C., and the solution was allowed to stand at this temperature. Precipitated crystal was separated and dried to give crude salt (30.02 g). The crude salt was recrystallized twice from 6.7 parts and then 5.5 parts of 100%-ethanol. 12.12 g of Purified salt was obtained (yield: 30%).

Melting point: 184.0–187.5° C.; $[\alpha]_D^{25}$+60.6° (c 0.51, EtOH); IR (cm$^{-1}$) 3400–3200, 3200–2800, 1608, 1575, 1530, 1381, 860, 812, 747. $^1$H-NMR (DMSO) δ (ppm) 1.43 (d, 3H); 4.28 ((I, 1H); 4.71 (s, 1H); 7.31–7.58; 7.77–7.86 (m, 12H).

The purified salt obtained was decomposed by addition of 3N-hydrochloric acid, and the decomposition mixture was subjected to extraction with ether. The separated ether phase was dried over anhydrous sodium sulfate, and the solvent was distilled off. Crude (S)-2-naphthylglycolic acid (7.22 g) was obtained in the form of white crystal. The crude product was recrystallized from a mixed solvent of chloroform (30 mL) and ethanol (5 mL) to give purified (S)-2-naphthylglycolic acid (6.05 g, yield: 24%, optical purity: 99% e.e. or higher).

Melting point: 163.5–167.0° C.; $[\alpha]_D^{25}$+145.9° (c 0.99, EtOH) IR (cm$^{-1}$) 3600–2200, 1690, 1400, 1285, 862, 828, 747. $^1$H-NMR (DMSO) δ (ppm) 3.35 (brs, 1H); 5.21 (s, 1H); 7.49–7.58 (m, 3H); 7.88–7.94 (m, 4H).

We claim:

1. A process for preparing an optically active 1-arylalkylamine, comprising the steps of:

combining a racemic 1-arylalkylamine expressed by the formula Ia:

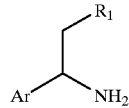

Ia wherein, $R_1$ is a hydrogen atom, a $C_1$–$C_5$ straight or branched chain alkyl or alkyloxy group, or phenyl group, wherein the phenyl group is optically substituted with one or more of a $C_1$–$C_5$ straight or branched chain alkyl or alkyloxy group, chlorine atom, bromine atom, iodine atom or nitro group;

Ar is a group of one of the following formulas:

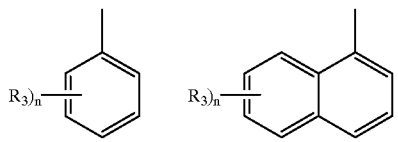

wherein $R_3$ is a $C_1$–$C_5$ straight or branched chain alkyl or alkyloxy group, chlorine atom, bromine atom, iodine atom or nitro group and n is zero, one or two;

with an optically active 1-naphthylglycolic acid or 2-naphthylglycolic acid, or one of their derivatives expressed by formula II below:

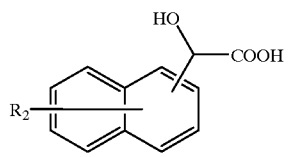

II wherein $R_2$ is one or more of a $C_1$–$C_5$ straight or branched chain alkyl or alkyloxy group, chlorine atom, bromine atom, iodine atom, or nitro group;

and then decomposing a diastereomer salt thus obtained to isolate an optically active 1-arylalkylamine.

2. A process for preparing an optically active 2-arylalkylamines, comprising the steps of: combining a racemic 2-arylalkylamine expressed by formula Ib or Ic:

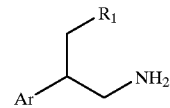

Ib

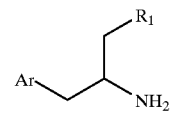

Ic wherein Ar and $R_1$ have the meaning defined above;

with an optically active 1-naphthylglycolic acid or 2-naphthylglycolic acid, or one of their derivatives, expressed by the general formula II below:

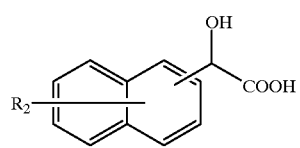

II wherein $R_2$ has the meaning defined above; and then, decomposing a diastereomeric salt thus obtained to isolate an optically active 2-arylalkylamine.

3. The process for preparing an optically active 1-arylalkylamine according to claim 1, wherein the combination is carried out in a medium selected from a lower alcohol; water; ethers; ketones; and a mixture of theses solvents.

4. The process for preparing an optically active 1-arylalkylamine according to claim 1, wherein the racemate of a 1-arylalkylamine of formula Ia is combined with one of optically active 1-naphthylglycolic acids or optically active 2-naphthylglycolic acids, or one of their derivatives, expressed by the general formula II in a molar ratio of Ia: II=1:0 to 1.2.

5. The process for preparing an optically active 2-arylalkylamine according to claim 2, wherein the combinatior is carried out in a medium selected from a lower alcohol; water; ethers; ketones; and a mixture of these solvents.

6. The process for preparing an optically active 2-arylalkylamine according to claim 2, wherein the racemate of 2-arylalkylarnine of formula Ib or Ic is combined with one of The optically active 1-naphthylglycolic acids or the optically active 2-naphthylglycolic acids, or one of their derivatives, expressed by the general formula II in a molar ratio of Ib, Ic: II=1:0.2 to 1.2.

* * * * *